United States Patent [19]

Su et al.

[11] Patent Number: 4,581,225
[45] Date of Patent: Apr. 8, 1986

[54] SUSTAINED RELEASE INTRANASAL FORMULATION AND METHOD OF USE THEREOF

[75] Inventors: Kenneth S. E. Su, Indianapolis; Kristina M. Campanale, Noblesville; Harve C. Wilson, Martinsville, all of Ind.

[73] Assignee: Eli Lilly and Company, Indianapolis, Ind.

[21] Appl. No.: 695,491

[22] Filed: Jan. 28, 1985

Related U.S. Application Data

[63] Continuation-in-part of Ser. No. 603,808, Apr. 25, 1984, abandoned.

[51] Int. Cl.⁴ .................. A61K 9/12; A61K 9/72; A61K 31/135
[52] U.S. Cl. .................................................. 424/45
[58] Field of Search ........................................... 424/45

[56] References Cited

U.S. PATENT DOCUMENTS

| | | | |
|---|---|---|---|
| 3,039,929 | 6/1962 | Stanko | 424/45 |
| 3,069,319 | 12/1962 | Stearns et al. | 424/45 |
| 3,106,511 | 10/1963 | Cuttler et al. | 424/45 |
| 3,155,574 | 11/1964 | Silson et al. | 424/45 |
| 3,159,535 | 12/1964 | Sesso et al. | 424/45 |
| 3,219,533 | 11/1965 | Mullins | 424/45 |
| 3,282,781 | 11/1966 | Macek et al. | 424/45 |
| 3,304,230 | 2/1967 | Abramson et al. | 424/45 |
| 3,320,125 | 5/1967 | Grim | 424/45 |
| 3,322,625 | 5/1967 | Shimmin | 424/45 |
| 3,406,237 | 10/1968 | Zeile et al. | 424/45 |
| 3,419,658 | 12/1968 | Sanders | 424/45 |
| 3,482,015 | 12/1969 | Bollinger et al. | 424/45 |
| 3,608,065 | 9/1971 | Lover et al. | 424/45 |
| 3,671,625 | 6/1972 | Altounyan | 424/45 |
| 3,987,200 | 10/1976 | Tuttle et al. | 424/330 |
| 4,001,391 | 1/1977 | Feinstone et al. | 424/45 |
| 4,016,279 | 4/1977 | Bauer et al. | 424/45 |
| 4,175,128 | 11/1979 | Taylor | 424/45 |
| 4,284,648 | 8/1981 | Hussain et al. | 424/330 |
| 4,385,048 | 5/1983 | Mygind et al. | 424/45 |

Primary Examiner—Shep K. Rose
Attorney, Agent, or Firm—Bruce J. Barclay; Arthur R. Whale

[57] ABSTRACT

Administration of a catecholamine by a novel intranasal delivery system provides prolonged blood levels of the drug.

10 Claims, 3 Drawing Figures

Figure 3

SUSTAINED RELEASE INTRANASAL FORMULATION AND METHOD OF USE THEREOF

CROSS REFERENCE TO RELATED APPLICATION

This is a continuation-in-part of Ser. No. 603,808, filed Apr. 25, 1984, now abandoned.

BACKGROUND OF THE INVENTION

Catecholamines are a class of chemical compounds known for their cardiotonic activity. Dobutamine is one of the most potent compounds of the class. Dobutamine is principally used in the short-term treatment of low output acute heart failure which may occur after myocardial infarction or after cardiopulmonary bypass surgery. Dobutamine is very rapidly biotransformed by catechol-O-methyltransferase. Since the compound has a half-life of only 2 minutes in the body, the drug currently must be given by continuous intravenous infusion. This method of administering the drug requires careful monitoring, and typically admission of the subject to a hospital. Because of the short life of the compound, an oral route of administration is impractical.

The present invention relates to an intranasal sustained release formulation of a catecholamine, such as dobutamine, which has been found to afford prolonged blood levels of such compounds in a warm-blooded animal. A sustained inotropic effect has also been observed. The present formulation has the added advantage of being easily administered to the patient generally without hospital admittance.

SUMMARY OF THE INVENTION

The present invention provides a sustained release intranasal formulation comprising a catecholamine, sustained release agent, and an emulsifying agent suspended in a suitable dispersion medium.

This invention also relates to a method for increasing cardiac contractibility in a warm-blooded animal in need of such therapy comprising administering to said animal a therapeutically effective amount of a sustained release intranasal formulation of the invention.

DETAILED DESCRIPTION OF THE INVENTION

Amounts and percentages are described herein in weight units unless stated otherwise.

The term "$C_1$–$C_4$ alkyl" represents a straight or branched alkyl chain having from one to four carbon atoms. Typical $C_1$–$C_4$ alkyl groups include methyl, ethyl, n-propyl, isopropyl, n-butyl, isobutyl, sec-butyl and t-butyl.

The term "$C_8$–$C_{10}$ alkyl" represents a straight or branched alkyl chain having either 8, 9 or 10 carbon atoms. Typical $C_8$–$C_{10}$ alkyl groups include n-octyl, isooctyl, n-nonyl, isononyl, n-decyl, isodecyl and the like.

The term "$C_8$–$C_{10}$ alkenyl" represents a straight or branched alkenyl chain having one or more carbon-carbon double bonds. Typical $C_8$–$C_{10}$ alkenyl groups include 5-octenyl, 1,3-octadienyl, 1,3,5-octatrienyl, 3,6-nonadienyl, 6-nonenyl, 5-decenyl, 4,8-decadienyl and the like.

The active ingredient employed in the present composition is a catecholamine, preferably dobutamine. The active ingredient will be present in the composition at a concentration at about 0.5 to about 20.0 percent by weight, preferably at a concentration in the range of about 2.0 to about 10.0 percent by weight.

Dobutamine is the generic name given to the preferred active ingredient employed in the present composition. The term "dobutamine", as defined herein, is intended to encompass any pharmaceutically acceptable form of the drug, for example either the free base or preferably a pharmaceutically acceptable acid addition salt thereof with mineral acids. Exemplary salts of this type include those prepared with phosphoric acid, sulfuric acid, hydrobromic acid and preferably hydrochloric acid. Dobutamine has the chemical name (+,−) 4-[2-[[3-(p-hydroxyphenyl)-1-methylpropyl]amino]ethyl]pyrocatechol, and may be represented by the following chemical structure:

Processes for preparing dobutamine, as well as a detailed description of its use, are taught in U.S. Pat. No. 3,987,200, herein incorporated by reference.

Other catecholamines which are contemplated for use in the present formulation include the following:

| Compound | $R_1$ | $R_2$ | $R_3$ |
|---|---|---|---|
| norepinephrine | OH | H | H |
| epinephrine | OH | H | $CH_3$ |
| isoproterenol | OH | H | $CH(CH_3)_2$ |

-continued

| Compound | $R_1$ | $R_2$ | $R_3$ |
|---|---|---|---|
| dopamine | H | H | H |
| methyl-dopamine | H | H | $CH_3$ |
| ethyl-dopamine | H | H | $CH_2CH_3$ |
| propyl-dopamine | H | H | $CH_2CH_2CH_3$ |
| isopropyl-dopamine | H | H | $CH(CH_3)_2$ |
| α-methyl-isopropyl-dopamine | H | $CH_3$ | $CH(CH_3)_2$ |
| α-ethyl-isopropyl-dopamine | H | $CH_2CH_3$ | $CH(CH_3)_2$ |
| cyclopropyl-dopamine | H | H | cyclopropyl |
| sec.-butyl-dopamine | H | H | $CH(CH_3)CH_2CH_3$ |
| phenyl-ethyl-dopamine | H | H | $CH_2CH_2\text{-Ph}$ |
| phenyl-isopropyl-dopamine | H | H | $CH(CH_3)CH_2\text{-Ph}$ |
| phenyl-sec.-butyl-dopamine | H | H | $CH(CH_3)CH_2CH_2\text{-Ph}$ |
| hydroxyphenyl-ethyl-dopamine | H | H | $CH_2CH_2\text{-Ph-OH}$ |
| hydroxyphenyl-isopropyl-dopamine | H | H | $CH(CH_3)CH_2\text{-Ph-OH}$ |
| hydroxyphenyl-ethyl-α-methyl-dopamine | H | $CH_3$ | $CH_2CH_2\text{-Ph-OH}$ |
| hydroxyphenyl-propyl-dopamine | H | H | $CH_2CH_2CH_2\text{-Ph-OH}$ |

The active agent employed herein may also exist as a combination of one or more of the catecholamines as defined above. An exemplary combination of this type includes dobutamine and dopamine.

The sustained release agent employed in the present intranasal formulation will be an oil or liquid at room temperature, that is, at a temperature of about 25° C. This agent is a compound of the formula $$R^1-CH=CH(CH_2)_7CO_2R^2$$

wherein
$R^1$ is $C_8-C_{10}$ alkyl or $C_8-C_{10}$ alkenyl; and
$R^2$ is hydrogen or $C_1-C_4$ alkyl.

Exemplary sustained release agents suitable for use in the present formulation include the following:

| trivial name | formula |
|---|---|
| linoleic acid | $CH_3(CH_2)_4CH=CHCH_2CH=CH(CH_2)_7\text{-}CO_2H$ |
| linolenic acid | $CH_3(CH_2CH=CH)_3(CH_2)_7CO_2H$ |
| ethyl linoleate | $CH_3(CH_2)_4CH=CHCH_2CH=CH(CH_2)_7\text{-}CO_2CH_2CH_3$ |
| methyl linolenate | $CH_3(CH_2CH=CH)_3(CH_2)_7CO_2CH_3$ |
| ethyl oleate | $CH_3(CH_{27})CH=CH(CH_2)_7CO_2CH_2CH_3$ |

The preferred sustained release agent employed in the present intranasal formulation is oleic acid. Oleic acid has the following structural formula:

$$CH_3(CH_2)_7CH=CH(CH_2)_7CO_2H$$

This compound may be obtained by the hydrolysis of various animal and vegetable fats and oils. The compound is more readily available commercially and its synthesis has been well documented in the literature. See, e.g., Robinson et al. in *J. Chem. Soc.* 127, 175 (1925).

The sustained release agent as defined above may also exist as a combination of more than one of the specific agents as herein described. Typical combinations would include oleic acid and linoleic acid, oleic acid and linolenic acid, oleic acid and ethyl oleate, methyl linoleate and methyl linolenate, and other like combinations in ratios so as to provide the desired sustained release effect.

The amount of sustained release agent employed herein will be from about 0.5 to about 50.0 percent by weight, more preferably about 2.0 to about 10.0 percent by weight of the formulation.

One or more emulsifying agents are added to the composition in order to improve its stability. The emulsifier employed may be chosen from among those generally known to be suitable for use in pharmaceutical formulations. Typical emulsifiers employed herein include the synthetic emulsifying agents. Depending on the charge possessed by the surfactant, this group may be divided into anionic, cationic, and nonionic types. The preferred emulsifier will be nonionic, and in particular a polyoxyethylene derivative. This type of emulsifier is commercially available under the trademark Tween. The most highly preferred emulsifier employed herein is Tween 85, which is polyoxyethylene 20 sorbitan trioleate, and is available from ICI Americas. Other suitable emulsifiers include the poloxamers including the Pluronic emulsifiers from BASF Wyandotte such as Pluronic L81. Blends of emulsifiers are common and may also be used herein. The reader is referred to REMINGTON PHARMACEUTICAL SCIENCES, Chapter 21, 16th Edition (1980) for a general discussion of suitable types of emulsifiers and their uses. The amount of emulsifier employed herein will be in the range of about 0.005 to about 5.0 percent by weight, more preferably at a rate in the range of about 0.1 to about 0.2 percent by weight of the formulation.

A dispersion medium will also be used in the present sustained release intranasal composition. This medium may be composed of a variety of substances such as water, alcohols and other like substantially non-toxic materials. However, this medium is preferably composed of one or more substances also capable of acting as a propellant for the system. Exemplary substances capable of being used herein include the Freons from E. I. DuPont de Nemours and Company such as Freon 114 (1,2-dichloro-1,1,2,2-tetrafluoroethane), Freon 12 (dichlorodifluoromethane) and Freon 11 (trichlorofluoromethane). The substances are preferably used in combination. While a variety of ingredients in assorted concentrations may be employed in the combinations, preferred combinations include about a 1:1 mixture of Freon 11 and Freon 12 by weight and about a 5:4:1 mixture of Freons 11:12:114 by weight. The amount of ingredients comprising the dispersion medium will be from about 40.0 to about 97.0 percent by weight, more preferably from about 80.0 to about 95.0 percent by weight of the total formulation.

One or more compounds having antioxidant properties are preferably used in the present composition to provide additional stability to the system. Suitable antioxidants include Vitamin E and particularly butyrated hydroxy anisole (BHA). When employed herein, the compound will be present at a concentration in the range of from about 0.001 to about 0.5 percent by weight of the composition, more preferably from about 0.1 to about 0.5 percent by weight.

Due to the nasal route of administration required for the present formulation, a scenting agent may also be added thereto if desired. When used herein the scenting agent will be present in the range of about 0.001 to about 1.0 percent by weight. Exemplary scenting agents include peppermint oil, lemon oil, olive oil and other like substances having a soothing effect on the olfactory system.

The formulations of the present invention may be prepared by procedures well known to those skilled in the art of formulation chemistry. Preferably the formulations are prepared as follows. The active ingredient employed herein is preferably micronized with any one of several devices employed in the art such as a mechanical micronizer prior to formulating. The particles should be in the range of about 0.1 to about 100 microns in diameter. Next, a stock solution is prepared by dissolving the emulsifying agent and any scenting agent or antioxidant into the sustained release agent. This mixture is thoroughly mixed, typically at room temperature, and combined with the active ingredient in a suitable cannister or container. The cannister may be metal or glass and is typical of those employed in the art for this purpose and capable of being pressurized. The cannister is then charged with one or more propellants as taught herein while cooling the cannister to a temperature in the range of from about 5° C. to about −50° C. more preferably from about 0° C. to about −20° C. The cannister is then sealed, typically with an aerosol type valve, and warmed to determine if there is leakage of the cannister. The formulation thus prepared is then suitable for administration to a warm-blooded animal in need of therapy requiring an increase in cardiac contractility.

A particularly preferred sustained release composition of the invention is as follows:

| Formula 1 | |
|---|---|
| Ingredient | Concentration (percent by weight) |
| dobutamine hydrochloride | about 2.0–4.0 |
| sustained release agent | about 2.0–12.0 |
| emulsifier | about 0.01–0.1 |
| antioxidant | about 0.05–0.2 |
| dispersion medium | about 80.0–93.9 |

More highly preferred compositions of the present invention may be represented by the following:

| Ingredient | Concentration (percent by weight) |
|---|---|
| Formula 2 | |
| dobutamine hydrochloride | about 2.0 |
| oleic acid | about 4.0 |
| Tween 85 | about 0.01 |
| BHA | about 0.1 |
| Freon 11 | about 46.945 |
| Freon 12 | about 46.945 |
| | 100.00 |
| Formula 3 | |
| dobutamine hydrochloride | about 2.0 |
| oleic acid | about 10.0 |
| Tween 85 | about 0.05 |
| BHA | about 0.1 |
| Freon 11 | about 43.925 |
| Freon 12 | about 43.925 |
| | 100.00 |
| Formula 4 | |
| dobutamine hydrochloride | about 2.0 |
| oleic acid | about 10.0 |
| Tween 85 | about 0.1 |
| BHA | about 0.1 |
| peppermint oil | about 0.3 |
| Freon 11 | about 43.75 |
| Freon 12 | about 43.75 |
| | 100.00 |
| Formula 5 | |
| dobutamine hydrochloride | about 4.0 |
| oleic acid | about 10.0 |
| Tween 85 | about 0.1 |
| BHA | about 0.1 |
| Freon 11 | about 42.9 |
| Freon 12 | about 34.32 |
| Freon 114 | about 8.58 |
| | 100.00 |

The following Examples illustrate specific sustained release intranasal compositions of the invention and methods for their preparation. The Examples are not intended to be limiting to the scope of the invention in any respect and should not be so construed.

EXAMPLE 1

Five hundred and sixty milligrams (4% by weight) of dobutamine hydrochloride were micronized in a mechanical micronizer to provide particles with a diameter of approximately 2 to 3 microns. A stock solution was prepared by dissolving 140 mg of BHA, 141 mg of Tween 85, 420 mg of peppermint oil and 700 mg of Pluronic L81 in 14.0 g of oleic acid at room temperature. The micronized dobutamine hydrochloride and 1.56 g (11.12% by weight) of the stock solution were added to an aerosol cannister. The cannister was previously cleaned by blowing pure nitrogen gas in the can while it was in an inverted position. The cannister was cooled to 0° C. and charged with 5.95 g (42.41% by weight) of Freon 11 and 5.96 g (42.48% by weight) of Freon 12. A valve was immeditely added and sealed onto the cannister. The cannister was placed in a hot water bath for several minutes to allow the contents to reach room temperature. The cannister was checked for leaks. The cannister was dried and activated several times to prime the valve. The valve was then protected with a suitable cap and the cannister was labeled and stored until ready for use.

The following Examples were prepared by the general procedure outlined in Example 1.

EXAMPLE 2

|  | percent by weight | weight (g) |
| --- | --- | --- |
| dobutamine hydrochloride | 0.50 | 0.14 |
| oleic acid | 1.16 | 0.34 |
| Tween 85 | 0.24 | 0.07 |
| Freon 11 | 5.3 | 1.55 |
| Freon 12 | 46.4 | 13.58 |
| Freon 114 | 46.4 | 13.58 |
|  | 100.0 |  |

EXAMPLE 3

|  | percent by weight | weight (g) |
| --- | --- | --- |
| dobutamine hydrochloride | 1.0 | 0.14 |
| oleic acid | 2.0 | 0.28 |
| Tween 85 | 0.5 | 0.07 |
| Freon 11 | 48.25 | 6.75 |
| Freon 12 | 48.25 | 6.75 |
|  | 100.0 |  |

EXAMPLE 4

|  | percent by weight | weight (g) |
| --- | --- | --- |
| dobutamine hydrochloride | 1.0 | 0.142 |
| oleic acid | 10.00 | 1.404 |
| Tween 85 | 0.58 | 0.081 |
| Freon 11 | 44.14 | 6.205 |
| Freon 12 | 44.28 | 6.224 |
|  | 100.0 |  |

EXAMPLE 5

|  | percent by weight | weight (g) |
| --- | --- | --- |
| dobutamine hydrochloride | 0.86 | 0.142 |
| oleic acid | 8.5 | 1.4 |
| Tween 85 | 0.5 | 0.083 |
| Freon 11 | 37.61 | 6.201 |
| Freon 12 | 52.53 | 8.663 |
|  | 100.0 |  |

EXAMPLE 6

|  | percent by weight | weight (g) |
| --- | --- | --- |
| dobutamine hydrochloride | 0.96 | 0.14 |
| oleic acid | 9.64 | 1.403 |
| Tween 85 | 0.55 | 0.079 |
| Freon 11 | 42.61 | 6.202 |
| Freon 12 | 46.24 | 6.73 |
|  | 100.00 |  |

EXAMPLE 7

|  | percent by weight | weight (g) |
| --- | --- | --- |
| dobutamine hydrochloride | 2.0 | 0.282 |
| oleic acid | 10.12 | 1.42 |
| Tween 85 | 0.55 | 0.077 |
| Freon 11 | 43.63 | 6.12 |
| Freon 12 | 43.70 | 6.13 |
|  | 100.0 |  |

EXAMPLE 8

|  | percent by weight | weight (g) |
| --- | --- | --- |
| dobutamine hydrochloride | 4.0 | 0.561 |
| oleic acid | 10.0 | 1.402 |
| Tween 85 | 0.51 | 0.072 |
| Freon 11 | 42.76 | 5.993 |
| Freon 12 | 42.73 | 5.987 |
|  | 100.0 |  |

EXAMPLE 9

|  | percent by weight | weight (g) |
| --- | --- | --- |
| dobutamine hydrochloride | 2.01 | 0.282 |
| oleic acid | 10.01 | 1.403 |
| Tween 85 | 0.5 | 0.07 |
| Freon 11 | 43.73 | 6.125 |
| Freon 12 | 43.75 | 6.130 |
|  | 100.0 |  |

EXAMPLE 10

|  | percent by weight | weight (g) |
| --- | --- | --- |
| dobutamine hydrochloride | 2.0 | 0.281 |
| oleic acid | 10.00 | 1.408 |
| Tween 85 | 0.54 | 0.076 |
| Freon 11 | 43.34 | 6.10 |
| Freon 12 | 44.12 | 6.211 |
|  | 100.0 |  |

EXAMPLE 11

|  | percent by weight | weight (g) |
| --- | --- | --- |
| dobutamine hydrochloride | 3.96 | 0.561 |
| oleic acid | 9.89 | 1.4 |
| Tween 85 | 0.51 | 0.073 |
| Freon 11 | 42.35 | 5.996 |
| Freon 12 | 43.29 | 6.129 |
|  | 100.0 |  |

EXAMPLE 12

|  | percent by weight | weight (g) |
|---|---|---|
| dobutamine hydrochloride | 1.96 | 0.283 |
| oleic acid | 9.69 | 1.406 |
| Tween 85 | 0.49 | 0.071 |
| peppermint oil | 0.41 | 0.060 |
| Freon 11 | 42.03 | 6.098 |
| Freon 12 | 45.42 | 6.590 |
|  | 100.0 |  |

EXAMPLE 13

|  | percent by weight | weight (g) |
|---|---|---|
| dobutamine hydrochloride | 1.9 | 0.282 |
| oleic acid, BHA, Tween 85, peppermint oil | 9.93 | 1.472 |
| Pluronic L81 | 4.86 | 0.72 |
| Freon 11 | 41.15 | 6.096 |
| Freon 12 | 42.16 | 6.248 |
|  | 100.0 |  |

EXAMPLE 14

|  | percent by weight | weight (g) |
|---|---|---|
| dobutamine hydrochloride | 6.00 | 0.849 |
| oleic acid, BHA, Tween 85, peppermint oil | 10.41 | 1.471 |
| Pluronic L81 | 0.49 | 0.07 |
| Freon 11 | 43.34 | 5.814 |
| Freon 12 | 41.95 | 5.930 |
|  | 100.19 |  |

EXAMPLE 15

|  | percent by weight | weight (g) |
|---|---|---|
| dobutamine hydrochloride | 1.96 | 0.28 |
| oleic acid | 9.78 | 1.4 |
| butylated hydroxy anisole | 0.1 | 0.014 |
| Tween 85 | 0.1 | 0.014 |
| peppermint oil | 0.29 | 0.042 |
| Freon 11 | 44.02 | 6.3 |
| Freon 12 | 43.75 | 6.26 |
|  | 100.0 |  |

EXAMPLE 16

|  | percent by weight | weight (g) |
|---|---|---|
| dobutamine hydrochloride | 7.0 | 0.98 |
| oleic acid | 10.0 | 1.4 |
| BHA | 0.1 | 0.014 |
| Tween 85 | 0.1 | 0.014 |
| Pluronic L81 | 0.5 | 0.07 |
| Freon 11 | 41.15 | 5.76 |
| Freon 12 | 41.15 | 5.76 |
|  | 100.0 |  |

EXAMPLE 17

|  | percent by weight | weight (g) |
|---|---|---|
| dobutamine hydrochloride | 1.99 | 0.280 |
| oleic acid | 1.01 | 0.143 |
| Tween 85 | 0.1 | 0.014 |
| Pluronic L81 | 0.5 | 0.07 |
| Freon 11 | 47.9 | 6.75 |
| Freon 12 | 48.50 | 6.836 |
|  | 100.0 |  |

EXAMPLE 18

|  | percent by weight | weight (g) |
|---|---|---|
| dobutamine hydrochloride | 1.97 | 0.28 |
| oleic acid | 3.95 | 0.56 |
| Tween 85 | 0.14 | 0.02 |
| Pluronic L81 | 0.49 | 0.07 |
| Freon 11 | 46.07 | 6.54 |
| Freon 12 | 47.38 | 6.725 |
|  | 100.0 |  |

EXAMPLE 19

|  | percent by weight | weight (g) |
|---|---|---|
| dobutamine hydrochloride | 1.98 | 0.28 |
| oleic acid | 6.94 | 0.98 |
| Tween 85 | 0.11 | 0.016 |
| Pluronic L81 | 0.5 | 0.072 |
| Freon 11 | 44.85 | 6.329 |
| Freon 12 | 45.62 | 6.435 |
|  | 100.0 |  |

EXAMPLE 20

|  | percent by weight | weight (g) |
|---|---|---|
| dobutamine hydrochloride | 1.98 | 0.28 |
| oleic acid | 2.01 | 0.285 |
| Tween 85 | 0.12 | 0.017 |
| Pluronic L81 | 0.49 | 0.07 |
| Freon 11 | 47.16 | 6.683 |
| Freon 12 | 48.24 | 6.835 |
|  | 100.0 |  |

EXAMPLE 21

|  | percent by weight | weight (g) |
|---|---|---|
| dobutamine hydrochloride | 2.0 | 0.28 |
| oleic acid | 6.99 | 0.981 |
| Tween 85 | 0.11 | 0.015 |
| Freon 11 | 45.39 | 6.369 |
| Freon 12 | 45.51 | 6.386 |
|  | 100.0 |  |

EXAMPLE 22

|  | percent by weight | weight (g) |
|---|---|---|
| dobutamine hydrochloride | 1.99 | 0.28 |
| linoleic acid | 7.0 | 0.983 |
| BHA | 0.1 | 0.14 |
| Tween 85 | 0.1 | 0.14 |
| Freon 11 | 45.28 | 6.359 |
| Freon 12 | 45.53 | 6.394 |
|  | 100.0 |  |

EXAMPLE 23

|  | percent by weight | weight (g) |
|---|---|---|
| dobutamine hydrochloride | 1.87 | 0.28 |
| ethyl oleate | 9.39 | 1.402 |
| Tween 85 | 0.48 | 0.071 |
| Freon 11 | 40.99 | 6.123 |
| Freon 12 | 47.27 | 7.06 |
|  | 100.0 |  |

EXAMPLE 24

|  | percent by weight | weight (g) |
|---|---|---|
| dobutamine hydrochloride | 1.99 | 0.281 |
| ethyl oleate | 9.94 | 1.4 |
| Tween 85 | 0.55 | 0.078 |
| Freon 11 | 43.50 | 6.127 |
| Freon 12 | 44.02 | 6.2 |
|  | 100.0 |  |

EXAMPLE 25

|  | percent by weight | weight (g) |
|---|---|---|
| dobutamine hydrochloride | 1.99 | 0.281 |
| ethyl oleate | 9.95 | 1.403 |
| Tween 85 | 0.50 | 0.07 |
| Freon 11 | 43.43 | 6.126 |
| Freon 12 | 44.13 | 6.225 |
|  | 100.0 |  |

The present invention also provides a method for increasing cardiac contractility in a warm-blooded animal in need of such therapy comprising administering to said animal a therapeutically effective amount of a sustained release intranasal formulation of the invention. The term "therapeutically effective amount," as used herein, refers to an amount of a catecholamine formulated for intranasal sustained release capable of ameliorating a degenerative cardiac condition. Typically a catecholamine is administered as described herein at a rate in the range of about 175 mcg/kg to about 7 mg/kg in order to restore the contractile force of the heart muscle.

According to the present invention, it has been unexpectedly discovered that a catecholamine can be formulated for nasal administration and upon administration achieve equivalent bioavailability as compared to intravenous administration. The purpose of the following study is to examine the bioavailability of the catecholamine dobutamine when administered intranasally and intravenously.

Six male rats weighing 280 g were anesthetized with sodium pentobarbital (50 mg/kg I.P.). Three rats were dosed intravenously with dobutamine hydrochloride at 2.5 mg/kg. Blood samples were taken at 0.5, 2, 4, 6, 10, 15, 20 and 30 minutes for dobutamine plasma analysis. The three remaining rats received dobutamine at 2.5 mg/kg intranasally in a saline solution. Blood samples from these rats were taken at 1, 5, 10, 20, 30, 60 and 120 minutes.

Figure 1:
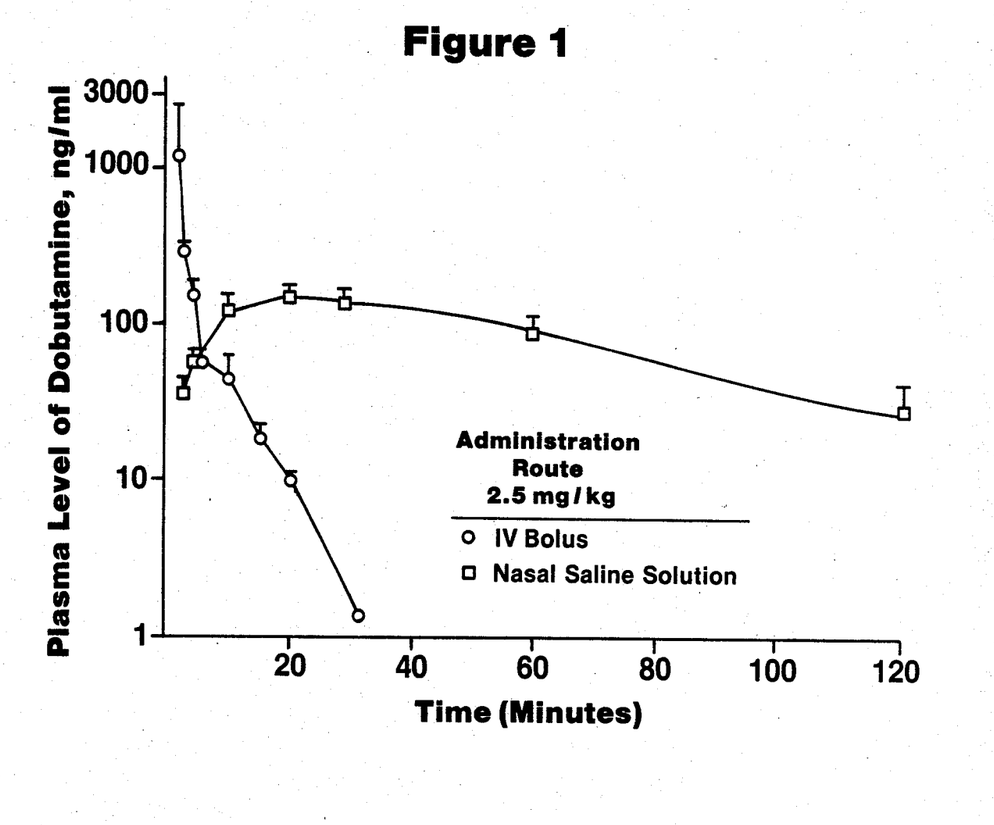
FIG. 1 is a semi-logarithmic plot of plasma levels of dobutamine hydrochloride in rats obtained when the drug was administered at a dose of 2.5 mg/kg. Dobutamine hydrochloride was administered by an intravenous bolus and by an intranasal saline solution. The graph represents the average of three trials.

FIG. 1 shows the results of the rat study described above as the average dobutamine plasma level produced by each method of administration over the duration of the study. As is known, the one time intravenous administration of dobutamine hydrochloride at 2.5 mg/kg produced a very high dobutamine blood level (greater than 1000 ng/ml) within 30 seconds after administration. The duration of dobutamine in the blood as a result of this method of administration was brief however, lasting only for a period of approximately 30 minutes. For comparison, 1.456 mg of dobutamine hydrochloride was dissolved in 0.2 ml of saline solution and 0.1 ml of this solution was administered intranasally to a 291 g rat to provide a dose of 2.5 mg/kg. This route of administration shows the prolonged effect afforded by intranasal delivery in comparison to the intravenous bolus administration. The intranasal delivery of dobutamine produced a moderate dobutamine blood level of 100 ng/ml after 20 minutes. Surprisingly, however, this effective blood level remained after two hours.

The area under the curve (AUC) was calculated with computer assistance employing the trapezoidal method for each route of administration. These results are reported below in Table I.

TABLE I

| Area Under the Curve After Intravenous Bolus and Intranasal Saline Solution Administration | |
|---|---|
| Route | AUC ng · min/ml |
| IV | 2223.3 ± 111.4 |
| Nasal | 11269 ± 1390.4 |

The following study was also conducted to evaluate the bioavailability of dobutamine hydrochloride formulated as a sustained release intranasal formulation of the invention. The following procedure represents the anesthetized dog study referred to herein.

Mongrel dogs of mixed sex weighing 8.0 to 20.0 kg were anesthetized with sodium thiopental (15 mg/kg, i.v.) and sodium phenobarbital (100 mg/kg, i.v.). A positive pressure pump provided ventilation through a cuffed endotracheal tube (18 strokes/min, 20 mg/kg/stroke) and a heating pad maintained the body temperature of the dog at 37°–38° C. Both vagus nerves were sectioned through an incision in the neck. Arterial blood pressure was monitored using a Statham pressure transducer attached to a cannula filled with heparinized saline (16 units/ml) inserted into the abdominal aorta via the right femoral artery. A cannula connected to a three-way stopcock was inserted in the right femoral vein for drug administration. The heart was exposed through the fifth right intercostal space and a precalibrated Walton-Brodie strain gauge arch was sutured on the right ventricle. The strain gauge was adjusted to a tension of 50 g at systole and a Beckman Dynograph recorder was set so that the 50 g tension produced a pen deflection of 10 mm. Heart rate was derived electronically from the blood pressure pulse using a Beckman cardiotachometer coupler.

Figure 2:
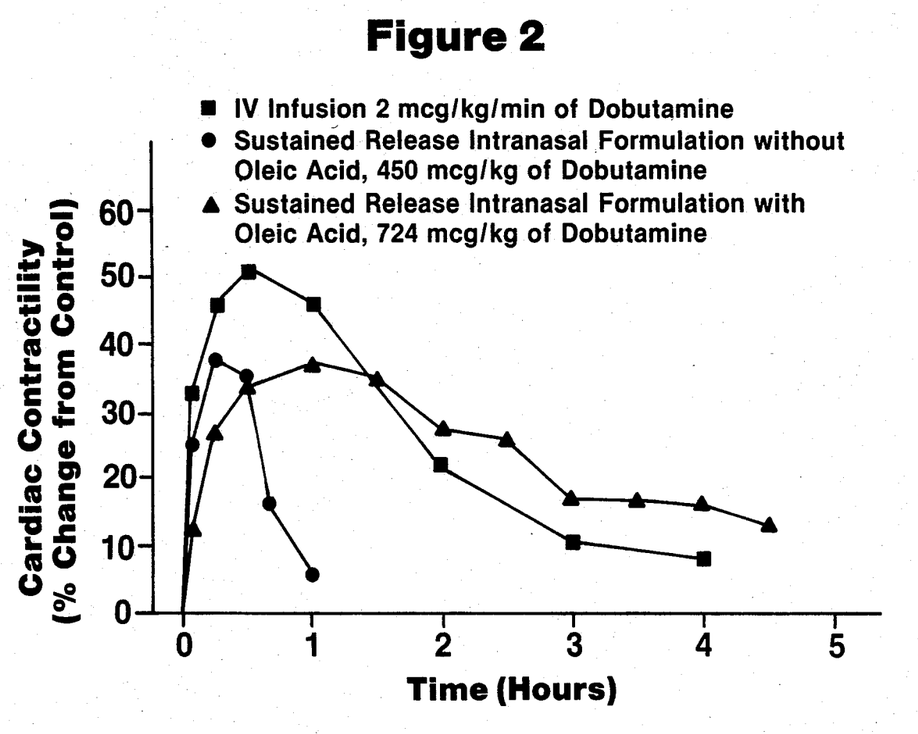
FIG. 2 compares an intravenous infusion of dobutamine hydrochloride with the prolonged release obtained by a sustained release intranasal composition of dobutamine hydrochloride with oleic acid and the same composition without oleic acid. This study represents one trial conducted in the anesthetized dog.
Figure 3:
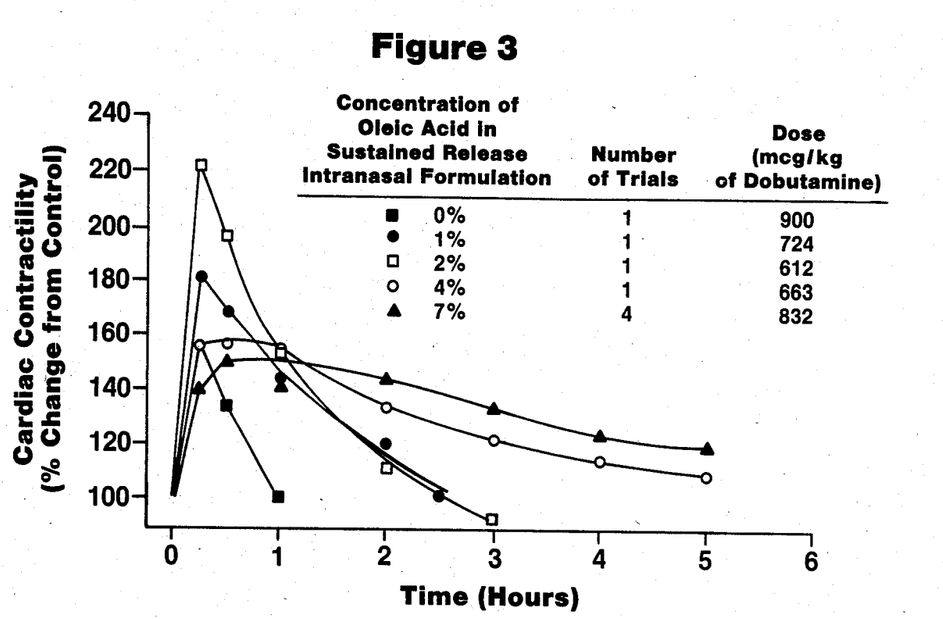
FIG. 3 shows the effect of various concentrations of oleic acid in a present sustained release formulation on the duration of cardiac contractility of dobutamine hydrochloride at various dose levels in anesthetized dogs after nasal administration.

FIGS. 2 and 3 above represent data obtained from the anesthetized dog study as described above.

FIG. 2 represents a comparison of the inotropic effect observed by the intravenous infusion of dobutamine hydrochloride at a rate of 2 mcg/kg/min with an intranasal formulation without oleic acid and an identical intranasal formulation except with oleic acid. The sustained release intranasal formulation without oleic acid was prepared by combining 0.420 g of dobutamine hydrochloride, 0.21 g of Tween 85, 20.685 g of Freon 11 and 20.685 g of Freon 12. The sustained release intranasal formulation with oleic acid is represented by Example 10 above. The results indicate that the pharmacodynamics of intravenous and intranasal sustained release routes of administration are similar. The oleic acid formulation provides a sustained release effect 4½ hours after administration.

FIG. 3 illustrates the dobutamine cardiac contractility responses produced by changing the concentration of oleic acid in a sustained release formulation of the invention. The formulation containing no oleic acid consisted of 0.420 g of dobutamine hydrochloride, 0.21 g of Tween 85, 20.685 g of Freon 11 and 20.685 g of Freon 12. The formulation containing 1% oleic acid by weight is represented by Example 17 and the formulation containing 2% oleic acid by weight is described in Example 20. Example 18 illustrates the formulation containing approximately 4% oleic acid while the formulation containing 7% oleic acid is described in Example 21. Two advantageous effects are apparent upon increasing the concentration of oleic acid in the composition from 0% to 7%. First, a prolonged response of cardiac contractility is observed as the amount of oleic acid is increased to a maximum duration of approximately 5 hours. Second, the initial dobutamine effect which manifests itself as a sharp peak during the first 30 minutes following administration is greatly reduced for the sustained release compositions containing both 4% and 7% oleic acid by weight.

We claim:

1. A sustained release intranasal formulation comprising from about 0.5 to about 20.0 percent by weight of a catecholamine, from about 0.005 to about 5.0 percent by weight of an emulsifying agent suspended in from about 40.0 to about 97.0 percent by weight of a suitable freon aerosol propellant dispersion medium and from about 0.5 to about 50.0 percent by weight of a sustained release agent of the formula $$R^1-CH=CH(CH_2)_7CO_2R^2$$

wherein
$R^1$ is $C_8$-$C_{10}$ alkyl or $C_8$-$C_{10}$ alkenyl; and
$R^2$ is hydrogen or $C_1$-$C_4$ alkyl.

2. A formulation of claim 1 wherein the catecholamine is dobutamine hydrochloride.

3. A formulation of claim 1 wherein the emulsifying agent is poloxyethylene 20 sorbitan trioleate.

4. A formulation of claim 1 wherein $R^1$ is $C_8$-$C_{10}$ alkyl.

5. A formulation of claim 4 wherein the sustained release agent is oleic acid.

6. A formulation of claim 1 wherein $R^1$ is $C_8$-$C_{10}$ alkenyl.

7. A formulation of claim 6 wherein the sustained release agent is linoleic acid.

8. A method for increasing cardiac contractibility in a warm-blooded animal in need of such therapy comprising administering to said animal a therapeutically effective amount of a sustained release intranasal formulation of claim 1.

9. A method of claim 8 wherein the intranasal formulat contains dobutamine as the catecholamine.

10. A method of claim 8 wherein the intranasal formulation contains oleic acid as the sustained release agent.

* * * * *